United States Patent
Viola

(10) Patent No.: US 8,142,475 B2
(45) Date of Patent: Mar. 27, 2012

(54) ADHESIVE SUTURE STRUCTURE AND METHODS OF USING THE SAME

(75) Inventor: Frank J. Viola, Sandy Hook, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 517 days.

(21) Appl. No.: 11/251,154

(22) Filed: Oct. 14, 2005

(65) Prior Publication Data

US 2006/0085036 A1    Apr. 20, 2006

Related U.S. Application Data

(60) Provisional application No. 60/620,141, filed on Oct. 18, 2004.

(51) Int. Cl.
*A61L 17/00* (2006.01)

(52) U.S. Cl. .......... 606/228; 606/229; 606/230; 606/231

(58) Field of Classification Search .......... 606/144–148, 606/224, 228–231; 604/181–206, 403–416; 623/1.42; 424/443
See application file for complete search history.

(56) References Cited

U.S. PATENT DOCUMENTS

| | | | | |
|---|---|---|---|---|
| 2,620,028 A | * | 12/1952 | Kohut | 163/5 |
| 3,212,502 A | * | 10/1965 | Myers | 606/224 |
| 3,474,703 A | * | 10/1969 | William et al. | 87/1 |
| 3,791,388 A | | 2/1974 | Hunter et al. | |
| 3,991,766 A | * | 11/1976 | Schmitt et al. | 606/230 |
| 4,024,871 A | * | 5/1977 | Stephenson | 606/231 |
| 4,159,720 A | * | 7/1979 | Burton | 424/423 |
| 5,735,829 A | | 4/1987 | Homesteel | |
| 4,981,149 A | | 1/1991 | Yoon et al. | |
| 5,269,807 A | | 12/1993 | Liu | |
| 5,306,289 A | | 4/1994 | Kaplan et al. | |
| 5,405,358 A | | 4/1995 | Liu et al. | |
| 5,456,696 A | | 10/1995 | Liu | |
| 5,456,697 A | | 10/1995 | Chesterfield et al. | |
| 5,480,411 A | * | 1/1996 | Liu et al. | 606/230 |
| 5,542,594 A | | 8/1996 | McKean et al. | |
| 5,569,302 A | * | 10/1996 | Proto et al. | 606/228 |
| 5,643,295 A | | 7/1997 | Yoon | |
| 5,665,109 A | | 9/1997 | Yoon | |
| 5,725,557 A | | 3/1998 | Gatturna et al. | |
| 5,763,411 A | | 6/1998 | Edwardson et al. | |
| 5,799,857 A | | 9/1998 | Robertson et al. | |

(Continued)

FOREIGN PATENT DOCUMENTS

BE    905 947 A    4/1987

(Continued)

OTHER PUBLICATIONS

European Search Report for 05 80 4217 date of completion is Aug. 12, 2009 (3 pages).

(Continued)

*Primary Examiner* — Corrine M McDermott
*Assistant Examiner* — Mark Mashack

(57) ABSTRACT

According to an aspect of the present disclosure, a surgical suture needle assembly is provided including an elongate tube defining a lumen through at least a portion of a length thereof; and a wound treatment material contained within the lumen of the suture structure. The present disclosure further provides for methods of using the surgical suture needle assembly in anastomotic procedures and the like.

16 Claims, 4 Drawing Sheets

U.S. PATENT DOCUMENTS

| | | | |
|---|---|---|---|
| 5,915,616 A | 6/1999 | Viola et al. | |
| 5,919,473 A * | 7/1999 | Elkhoury | 424/422 |
| 5,964,394 A | 10/1999 | Robertson | |
| 6,011,121 A | 1/2000 | Goldmann et al. | |
| 6,032,849 A | 3/2000 | Mastri et al. | |
| 6,045,560 A | 4/2000 | McKean et al. | |
| 6,191,236 B1 | 2/2001 | Roby et al. | |
| 6,214,332 B1 | 4/2001 | Askill et al. | |
| 6,264,675 B1 * | 7/2001 | Brotz | 606/228 |
| 6,551,353 B1 * | 4/2003 | Baker et al. | 623/1.42 |
| 2002/0173770 A1 * | 11/2002 | Flory et al. | 604/537 |
| 2005/0070959 A1 * | 3/2005 | Cichocki | 606/223 |
| 2005/0125034 A1 * | 6/2005 | Cichocki | 606/222 |

FOREIGN PATENT DOCUMENTS

| | | |
|---|---|---|
| EP | 0 0531 742 A | 3/1993 |
| FR | 2 747 908 A | 10/1997 |
| WO | WO 03/088845 A | 10/2003 |
| WO | WO 03/105698 A | 12/2003 |
| WO | WO 2005/055836 A | 6/2005 |

OTHER PUBLICATIONS

International Search Report for PCT/US/05/36744 date of completion is Apr. 10, 2008 (8 pages).

* cited by examiner

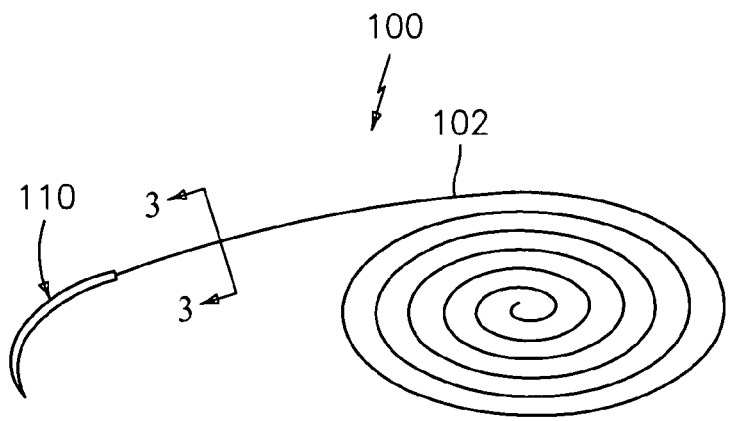
FIG. 2
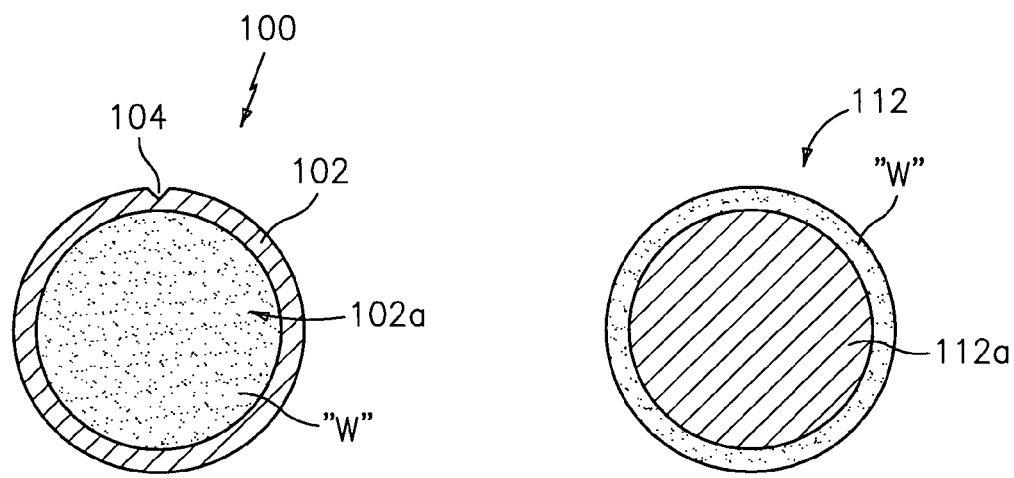
FIG. 3
FIG. 4
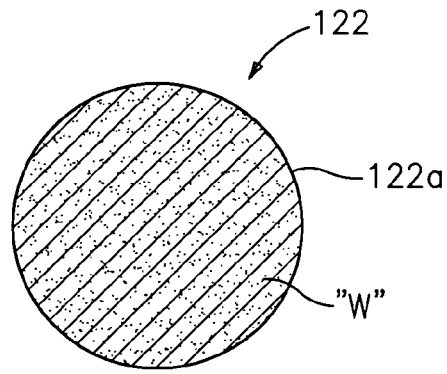
FIG. 5

ADHESIVE SUTURE STRUCTURE AND METHODS OF USING THE SAME

CROSS-REFERENCE TO RELATED APPLICATION

The present application claims the benefit of and priority to U.S. Provisional Application Ser. No. 60/620,141, filed on Oct. 18, 2004, the entire disclosure of which is incorporated herein by reference.

BACKGROUND

1. Technical Field

The present disclosure relates generally to suture structures and methods of using the same and, more particularly, to suture structures containing a wound treatment material and the like and methods of using the same in anastomotic procedures and the like.

2. Discussion of Related Art

Throughout the years the medical field has utilized various techniques in an effort to join or bond body tissue together. Historically, suturing was the accepted technique for rejoining severed tissues and closing wounds. Suturing was historically achieved with a surgical needle and a suturing thread, and more recently, with a variety of polymeric or metallic staples, as will be discussed below. The intended function of sutures is to hold the edges of a wound or tissue against one another during the healing process so as to reduce discomfort, pain, scarring and the time required for healing.

Recently, many procedures which in the past required conventional suturing have been replaced by staple suturing which involves the application of the staples to the edges of the wound or tissue with the use of a surgical stapler. Surgical staplers have been developed for joining adjacent tissue, for providing hemostasis of adjacent tissue and for providing hemostasis in conjunction with cutting of adjacent tissue. Such surgical staplers include both linear and annular type configurations. A typical linear stapler and cutter includes parallel rows of staples with a slot for a cutting means to travel between the rows of staples.

Typical linear type staplers are disclosed in commonly assigned U.S. Pat. No. 6,045,560 to McKean et al., U.S. Pat. No. 6,032,849 to Mastri et al., and U.S. Pat. No. 5,964,394 to Robertson, the entire contents of each of which are incorporated herein by reference. A typical annular stapler and cutter, including a plurality of annular rows of staples, typically two, and an annular blade disposed internal of the rows of staples, is disclosed in commonly assigned U.S. Pat. No. 5,799,857 to Robertson et al. and U.S. Pat. No. 5,915,616 to Viola et al., the entire contents of each of which are incorporated herein by reference.

These types of surgical staplers secure adjoining body tissue for improved cutting, join layers of tissue to one another and provide hemostasis by applying parallel or annular rows of staples to surrounding tissue as the cutting means cuts between the parallel or annular rows. Accordingly, by enabling a surgeon to perform all of these tasks simultaneously, surgical staplers have been effective in decreasing the amount of time it takes to fasten tissue together. To even further enhance joining and hemostasis in instances where the stapler is used in highly vascularized tissue, surgical staplers with multiple rows of staples have been used with a high degree of success.

Other surgical procedures utilize pledgets, buttresses or other types of reinforcement materials and fabrics. These buttresses are typically placed over the tissue contacting surface of the anvil and/or the tissue contacting surface of the cartridge of the surgical stapling instrument and secured against the target tissue during the firing of the surgical stapling instrument. Reference may be made to U.S. Pat. No. 5,542,594, the entire content of which is incorporated herein by reference, for a more detailed discussion of the use of buttresses in cooperation with surgical stapling instrument.

Still other surgical procedures involve the step of applying (e.g., by spraying, brushing, etc.) an adhesive material and/or a sealant material to the external surface of the target surgical site following the surgical stapling procedure.

Another procedure which has been developed includes the use of biological tissue adhesives have recently been developed for tissue repair and the creation of anastomoses. Generally, biological adhesives bond separated tissues together to aid in the healing process and to enhance the tissue strength. Such adhesives may be used instead of suturing and stapling for example in surgical procedures for the repair of tissue or the creation of anastomoses.

The application of a suitable biocompatible adhesive offers many advantages to the patient and the surgeon alike such as, for example, the avoidance of penetration of tissue by needles and/or staples, as well as the immediate sealing of the tissue being treated. Moreover, use of a biocompatible adhesive tends to minimize foreign body reaction and scarring. Despite these advantages, however, the weakness along the tissue seam remains as a primary disadvantage in the use of biocompatible adhesives.

Accordingly, the need exists for surgical sutures which reduce the trauma suffered by the patient, reduce the instances of leakage, reduce the instances of bleeding, and create a relatively strong bond between adjacent body tissues.

SUMMARY

The present disclosure relates to suture structures containing a wound treatment material and the like and methods of using the same in anastomotic procedures and the like.

According to an aspect of the present disclosure, a surgical suture needle assembly is provided including an elongate tube defining a lumen through at least a portion of a length thereof; and a wound treatment material contained within the lumen of the suture structure.

The wound treatment material desirably includes at least one of an adhesive, a hemostat, and a sealant. The adhesive may include at least one of a protein derived, aldehyde-based adhesive materials, and cyanoacrylate-based materials. The sealant may include at least one of a fibrin sealant, a collagen-based tissue sealant, a synthetic polymer-based tissue sealant, and synthetic polyethylene glycol-based, hydrogel materials. The hemostat may include at least one of a fibrin-based, collagen-based, oxidized regenerated cellulose-based and gelatin-based topical hemostats, and fibrinogen-thrombin combination materials. The wound treatment material may include a therapeutic agent which includes an antibiotic including at least one of gentamycin sulfate, erythromycin, and derivatized glycopeptides.

The wound treatment material may include at least one growth promoting factor. The growth promoting factor may include at least one of fibroblast growth factor, bone growth factor, epidermal growth factor, platelet derived growth factor, macrophage derived growth factor, alveolar derived growth factor, monocyte derived growth factor, and magainin.

The surgical suture needle assembly may further include a suture needle operatively connected to an end of the suture structure.

The suture structure may include at least one weakening element formed therein. Accordingly, in use, the suture structure ruptures upon application of a compressive force thereto, whereby the wound treatment material is released therefrom.

The suture structure may be fabricated from one of a bio-absorbable material and a non-absorbable material. The non-absorbable material of the suture structure may include at least one of silk, polyamides, polyesters, polyethylene terephthalate, polyacrylonitrile, polyethylene, polypropylene, silk cotton, and linen. The bio-absorbable material of the suture structure may include at least one of a natural collagenous material, and synthetic resins including those derived from glycolic acid, glycolide, lactic acid, lactide, dioxanone, polycaprolactone, epsilon-caprolactone, and trimethylene carbonate.

The suture structure may be a braid and the wound treatment material is imbedded in the braid.

According to another aspect of the present disclosure, a surgical suture needle assembly is provided including a suture structure; and a wound treatment material at least one of incorporated into and onto the suture structure.

According to the present embodiment, the suture structure may be fabricated from one of a bio-absorbable material and a non-absorbable material. The non-absorbable material of the suture structure may include at least one of silk, polyamides, polyesters, polyethylene terephthalate, polyacrylonitrile, polyethylene, polypropylene, silk cotton, and linen. The bio-absorbable material of the suture structure may include at least one of a natural collagenous material, and synthetic resins including those derived from glycolic acid, glycolide, lactic acid, lactide, dioxanone, polycaprolactone, epsilon-caprolactone, and trimethylene carbonate.

In the present embodiment, the suture structure may be a braid and the wound treatment material may be imbedded in the braid.

The wound treatment material may include at least one of an adhesive, a hemostat, and a sealant. The surgical suture needle assembly may further include a suture needle operatively connected to an end of the suture structure.

According to yet another embodiment of the present disclosure, a method of performing a surgical anastomosis procedure is provided. The method includes providing a surgical stapling apparatus having a body portion, a staple cartridge assembly supported on a distal end of the body portion, and an anvil assembly selectively connectable to a distal end of the body portion in juxtaposed relation to the staple cartridge assembly, and providing at least one suture needle assembly including a suture structure having a wound treatment material associated with the suture structure.

The method further includes the steps of inserting the anvil assembly into a first intestinal section; suturing, with a suture needle assembly, the first intestinal section, about a shaft of the anvil assembly such that at least a portion of the suture structure extends over a tissue contacting surface of the anvil assembly; inserting the distal end of the stapling apparatus into a second intestinal section; suturing, with another suture needle assembly, the second intestinal section to the staple cartridge assembly disposed at the distal end of the body portion of the stapling apparatus such that at least a portion of the suture structure extends into a tissue contacting surface of the staple cartridge assembly; and connecting the shaft of the anvil assembly to the distal end of the body portion.

The method still further includes the steps of approximating the anvil assembly toward the distal end of the body portion to capture the first and second intestinal sections therebetween and to release the wound treatment material from the suture structure.

The wound treatment material may include at least one of an adhesive, a hemostat, and a sealant.

According to an embodiment, the suture structure may include a lumen extending at least partially therethrough, wherein the wound treatment material is contained within the lumen of the suture structure. The wound treatment material may be incorporated into and/or onto the suture structure.

The adhesive may include at least one of a protein derived, aldehyde-based adhesive materials, and cyanoacrylate-based materials. The sealant may include at least one of a fibrin sealant, a collagen-based tissue sealant, a synthetic polymer-based tissue sealant, and synthetic polyethylene glycol-based, hydrogel materials. The hemostat may include at least one of a fibrin-based, collagen-based, oxidized regenerated cellulose-based and gelatin-based topical hemostats, and fibrinogen-thrombin combination materials.

The wound treatment material may further include a therapeutic agent. The therapeutic agent may include an antibiotic including at least one of gentamycin sulfate, erythromycin, and derivatized glycopeptides. The wound treatment material may still further include at least one growth promoting factor. The growth promoting factor may include at least one of fibroblast growth factor, bone growth factor, epidermal growth factor, platelet derived growth factor, macrophage derived growth factor, alveolar derived growth factor, monocyte derived growth factor, and magainin.

It is envisioned that the suture structure may be fabricated from one of a bio-absorbable material and a non-absorbable material. The non-absorbable material of the suture structure may include at least one of silk, polyamides, polyesters, polyethylene terephthalate, polyacrylonitrile, polyethylene, polypropylene, silk cotton, and linen. The bio-absorbable material of the suture structure may include at least one of a natural collagenous material, and synthetic resins including those derived from glycolic acid, glycolide, lactic acid, lactide, dioxanone, polycaprolactone, epsilon-caprolactone, and trimethylene carbonate.

BRIEF DESCRIPTION OF DRAWINGS

The accompanying drawings, which are incorporated in and constitute a part of this specification, illustrate embodiments of the disclosure and, together with a general description of the disclosure given above and the detailed description of the embodiments given below, serve to explain the principles of the disclosure, wherein:

FIG. 2 is a perspective view of a needle assembly including a suture structure according to an embodiment of the present disclosure;

FIG. 3 is a transverse cross-sectional view of the suture structure of FIG. 2 as taken through 3-3 of FIG. 2;

FIG. 4 is a transverse cross-sectional view of a suture structure according to another embodiment of the present disclosure;

FIG. 5 is a transverse cross-sectional view of a suture structure according to yet another embodiment of the present disclosure;

DETAILED DESCRIPTION OF EMBODIMENTS

Figure 1:
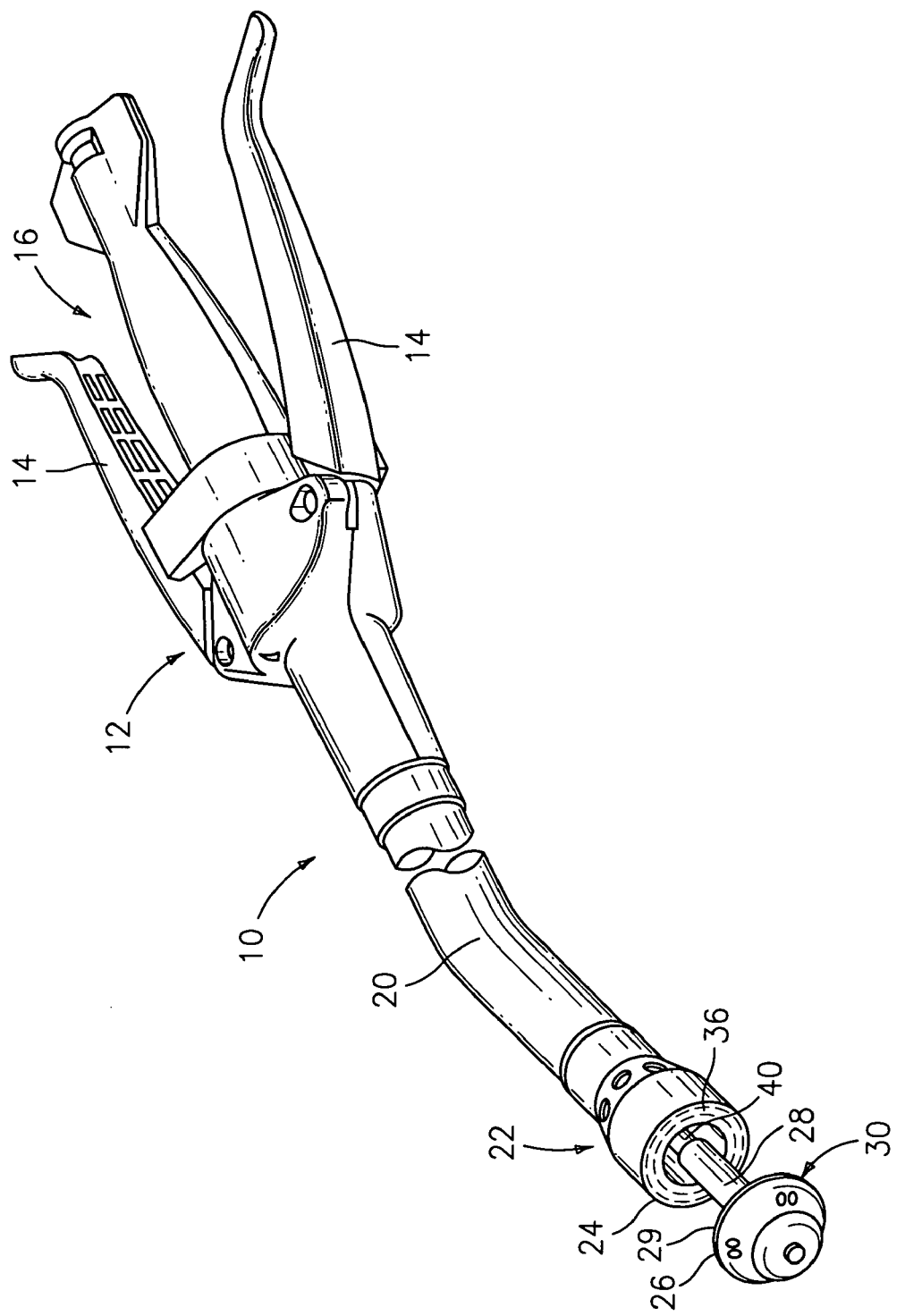
FIG. 1 is a perspective view of an exemplary prior art annular surgical stapling device.

Embodiments of the presently disclosed suture structure and methods of using the same when performing an annular anastomosis will now be described in detail with reference to the drawing figures wherein like reference numerals identify similar or identical elements. As used herein and as is traditional, the term "distal" refers to that portion which is furthest from the user while the term "proximal" refers to that portion which is closest to the user.

Referring initially to FIG. 1, an annular surgical stapling device, for use with the suture structures disclosed herein, is generally designated as 10. Surgical stapling device 10 includes a handle assembly 12 having at least one pivotable actuating handle member 14, and an advancing member 16. Extending from handle member 12, there is provided a tubular body portion 20 which may be constructed so as to have a curved shape along its length. Body portion 20 terminates in a staple cartridge assembly 22 which includes a pair of annular arrays of staple receiving slots 36 formed in a tissue contacting surface 24 thereof. Each staple receiving slot 36 having a staple 38 (see FIGS. 8 and 9) disposed therein. Positioned distally of staple cartridge assembly 22 there is provided an anvil assembly 30 including an anvil member 26 defining a tissue contacting surface 29, and a shaft 28 operatively associated therewith for removably connecting anvil assembly 30 to a connecting member 40 provided at a distal end portion of stapling device 10.

Staple cartridge assembly 22 may be fixedly connected to the distal end of tubular body portion 20 or may be configured to concentrically fit within the distal end of tubular body portion 20. Typically, staple cartridge assembly 22 includes a staple pusher 52 (see FIGS. 8 and 9) including a proximal portion having a generally frusto-conical shape and a distal portion defining two concentric rings of peripherally spaced fingers 52a, 52b (see FIGS. 8 and 9), each one of which is received within a respective staple receiving slot 36.

Typically, a knife 50 (see FIGS. 8 and 9), substantially in the form of an open cup with the rim thereof defining a knife edge, is disposed within staple cartridge assembly 22 and mounted to a distal surface of staple pusher 52. The knife edge is disposed radially inward of fingers 52a, 52b of staple pusher 52. Accordingly, in use, as staple pusher 52 is advanced, knife 50 is also advanced axially outward.

Reference may be made to U.S. Pat. No. 5,915,616 to Viola et al., the entire content of which is incorporated herein by reference, for a detailed discussion of the structure and use of annular stapling device 10.

Turning now to FIGS. 2 and 3, a suture needle assembly, including a suture structure in accordance with the present disclosure, is generally designated as 100. As seen in FIGS. 2 and 3, suture needle assembly 100 includes a suture structure 102, in the form of an elongate tube, defining a lumen 102a therethrough, and a wound treatment material "W" disposed and/or retained within lumen 102a thereof.

As seen in FIG. 3, it is contemplated that suture structure 102 may be provided with a weakening element 104 formed therein. For example, weakening element 104 may include and is not limited to, a line of reduced thickness extending along at least a portion of the length of suture structure 102, a series of segments of reduced thickness, a series of discrete pin-like weakening elements, and the like. Accordingly, in use, as a pressure on the exterior of suture structure 102 increases, due to, for example, the compression forces created by the approximation of anvil assembly 30 toward staple cartridge assembly 22, suture structure 102 will rupture along weakening element(s) 104 at lower compression forces as compared to an elongate tube having no weakening elements 104. Additionally, if the pressure within lumen 102a of suture structure 102 is increased, due to, for example, injecting more wound treatment material "W" into lumen 102a of suture structure 102, suture structure 102 will also rupture along weakening element(s) 104 at a force less than if no weakening element(s) 104 were provided.

Turning now to FIG. 4, in accordance with another embodiment of the present disclosure, a suture structure 112 is provided including an elongate core 112a which is at least partially coated with wound treatment material "W". Preferably, wound treatment material "W" is disposed or deposited around at least a portion of a perimeter of core 112a and along at least a portion of a length of core 112a.

Turning now to FIG. 5, in accordance with yet another embodiment of the present disclosure, a suture structure 122 is provided and includes an elongate core 122a, and a wound treatment material "W" dispersed throughout core 122a.

Turning back to FIG. 2, suture needle assembly includes a surgical needle 110 operatively connected to or secured to an end of any of suture structures 102, 112 or 122, disclosed herein, by any method known in the art.

Suture structures 102, 112 and 122 may be fabricated from a wide variety of natural and synthetic fibrous materials such as non-absorbable as well as partially and fully bio-absorbable (i.e., resorbable) natural and synthetic fiber-forming polymers. Non-absorbable surgical materials which are suitable for fabricating braided sutures include silk, polyamides, polyesters such as polyethylene terephthalate, polyacrylonitrile, polyethylene, polypropylene, silk cotton, linen, etc. Carbon fibers, steel fibers and other biologically acceptable inorganic fibrous materials can also be employed.

Desirably, suture structures 102, 112 and 122 are formed from absorbable surgical materials. For example, any of suture structures 102, 112 and 122 may be fabricated from natural collagenous material or synthetic resins including those derived from glycolic acid, glycolide, lactic acid, lactide, dioxanone, polycaprolactone, epsilon-caprolactone, trimethylene carbonate, etc., and various combinations of these and related monomers.

Additionally, suture structures 102, 112 and 122 may be fabricated from a block copolymer having one of the blocks made from hard phase forming monomers and another of the blocks made from random copolymers of soft phase forming monomers. Hard phase forming monomers include glycolide and lactide while soft phase forming monomers include 1,4 dioxane-2-one and 1,3 dioxane-2-one and caprolactone. Preferably, the block copolymers used in forming surgical articles include one block having glycolic acid ester units as a predominant component thereof. A "predominant component" is a component which is present in an amount greater than 50 mole percent. Exemplary block copolymers useful in forming surgical elements and, in particular, suture structures 102, 112 and 122, are described in U.S. Pat. No. 6,191,236, the entire contents of which are incorporated herein by reference.

The block copolymers may be formed into surgical articles (e.g., suture structures 102, 112 and 122) using any known technique, such as, for example, extrusion, molding and/or solvent casting. The copolymers can be used alone, blended with other absorbable compositions, or in combination with non-absorbable components. A wide variety of surgical articles may be manufactured from the copolymers described herein. These include, but are not limited to clips and other fasteners, staples, sutures, pins, screws, prosthetic devices, wound dressings, drug delivery devices, anastomotic rings, and other implantable devices. Fibers made from these copolymers may be knitted or woven with other fibers, either absorbable or non-absorbable to form sutures, meshes or fabrics. Additionally, compositions including these block copolymers may also be used as an absorbable coating for surgical devices. Preferably, however, the copolymers are spun into fibers to be used as sutures, either monofilament or multifilament.

Multifilament sutures made from the copolymers described herein can be prepared by methods known in the art. Additionally, braid constructions such as those described in U.S. Pat. Nos. 5,059,213 and 5,019,093, the entire contents of each of which being incorporated herein by reference, are suitable for the multifilament sutures disclosed herein.

Suitable apparatus for the manufacture of monofilament sutures from the block copolymers disclosed herein are described in U.S. Pat. No. 5,403,347, the disclosure of which is incorporated herein in its entirety by this reference.

It is envisioned that wound treatment material "W" may include and is not limited to one of or a combination of adhesives, hemostats, sealants. Surgical biocompatible wound treatment materials which can be disposed in support structure 102 or deposited on/in suture structures 112 or 122, include adhesives whose function is to attach or hold organs, tissues or structures, sealants to prevent fluid leakage, and hemostats to halt or prevent bleeding.

It is contemplated that the wound treatment material "W" may be a biocompatible sealant and/or adhesive, including, and not limited, to sealants which cure upon tissue contact, sealants which cure upon exposure to ultraviolet (UV) light, sealants which are two-part systems which are kept isolated from one another and are combined or any combinations thereof. In one embodiment, it is contemplated that such sealants and/or adhesives are curable. For example, the sealants and/or adhesives may have a cure time of from about 10 to 15 seconds may be used. In another embodiment, it is contemplated that a sealant and/or adhesive having a cure time of about 30 seconds may be used. In preferred embodiments, the sealant and/or adhesive is a bioabsorbable and/or bio-resorbable material.

In certain preferred embodiments, the wound treatment material "W" includes a sealant which is desirably a PEG-based material. Examples of classes of materials useful as the sealant and/or adhesive include acrylate or methacrylate functional hydrogels in the presence of a biocompatible photoinitiator, alkyl-cyanoacrylates, isocyanate functional macromers with or without amine functional macromers, succinimidyl ester functional macromers with amine or sulfhydryl functional macromers, epoxy functional macromers with amine functional macromers, mixtures of proteins or polypeptides in the presence of aldehyde crosslinkers, Genipin, or water-soluble carbodiimides, anionic polysaccharides in the presence of polyvalent cations, etc. Examples of sealants, which can be employed, include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies and Baxter International, Inc.

Surgical biocompatible wound treatment materials "W" which may be used in accordance with the present disclosure include adhesives whose function is to attach or hold organs, tissues or structures. Examples of adhesives which can be employed include protein derived, aldehyde-based adhesive materials, for example, the commercially available albumin/glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endo-surgery, Inc., respectively.

Some specific materials which may be utilized as adhesives include isocyanate terminated hydrophilic urethane prepolymers derived from organic polyisocyanates and oxyethylene-based diols or polyols, including those disclosed in U.S. Pat. Nos. 6,702,731 and 6,296,607 and U.S. Published Patent Application No. 2004/0068078; alpha-cyanoacrylate based adhesives including those disclosed in U.S. Pat. No. 6,565,840; alkyl ester based cyanoacrylate adhesives including those disclosed in U.S. Pat. No. 6,620,846; adhesives based on biocompatible crosslinked polymers formed from water soluble precursors having electrophilic and nucleophilic groups capable of reacting and crosslinking in situ, including those disclosed in U.S. Pat. No. 6,566,406; two part adhesive systems including those based upon polyalkylene oxide backbones substituted with one or more isocyanate groups in combination with bioabsorbable diamine compounds, or polyalkylene oxide backbones substituted with one or more amine groups in combination with bioabsorbable diisocyanate compounds as disclosed in U.S. Published Patent Application No. 2003/0032734, the contents of which are incorporated by reference herein; and isocyanate terminated hydrophilic urethane prepolymers derived from aromatic diisocyanates and polyols as disclosed in U.S. Published Patent Application No. 2004/0115229, the contents of which are incorporated by reference herein. It is contemplated that any known suitable adhesive may be used.

In certain embodiments, the wound treatment material "W" includes hemostats whose function it is to halt or prevent bleeding. Examples of hemostat materials, which can be employed, include fibrin-based, collagen-based, oxidized regenerated cellulose-based and gelatin-based topical hemostats, as well as aluminum alum (i.e., ammonium alum or aluminum ammonium sulfate). Examples of commercially available hemostat materials are fibrinogen-thrombin combination materials sold under the trade designations CoStasis™ by Tyco Healthcare Group, LP, and Tisseel™ sold by Baxter International, Inc. Hemostats herein include astringents, e.g., aluminum sulfate, and coagulants.

It is envisioned that wound treatment material "W" may be a relatively low viscosity fluid or liquid such that the wound treatment material "W" may freely flow from suture structure 102 upon rupturing thereof. It is further envisioned that wound treatment material "W" may include or be in the form of a fine powder of particulate material.

In other embodiments, wound treatment material "W" may include a medicament. The medicament may be disposed on structure 100 or impregnated into structure 100. The medicament may include one or more medically and/or surgically useful substances such as drugs, enzymes, growth factors, peptides, proteins, dyes, diagnostic agents or hemostasis agents, monoclonal antibodies, or any other pharmaceutical used in the prevention of stenosis. For example, SilvaSorb™ available from AcryMed, Inc., Portland, Oreg.

It is further contemplated that wound treatment material "W" may include, for example, compositions and/or compounds which accelerate or beneficially modify the healing process when particles of the composition and/or compound are applied to or exposed to a surgical repair site. For example, the wound treatment material "W" may be a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, wound treatment material "W" may include one or several growth promoting factors, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

Wound treatment material "W" may include visco-elastic film forming materials, cross-linking reactive agents, and energy curable adhesives. It is envisioned that wound treatment material "W", and in particular, adhesive may be cured with the application of water and/or glycerin (1,2,3-pranatetriol, also known as glycerol and glycerine) thereto. In this manner, the water and/or glycerin cure the adhesive and hydrate the wound.

It is further envisioned and within the of the present disclosure for wound treatment material "W" to include any microbial agent, analgesic, growth factor, and anti-inflammatory agent known by one having skill in the art or any combination thereof.

It is contemplated that it may be desirable to dye suture structures 102, 112, 122 in order to increase visibility of the suture structure in the surgical field. Dyes known to be suitable for incorporation in sutures can be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979). Preferably, suture structures 102, 112, 122 are dyed by adding up to about a few percent and preferably about 0.2% dye, and most preferably about 0.06% to about 0.08% dye, such as D&C Violet No. 2 to the resin prior to extrusion.

Turning now to FIGS. 6-9, there is illustrated the use of surgical stapling device 10, together with suture needle assembly 100 including suture structures 102, in an anastomosis procedure to effect joining of intestinal sections 66 and 68. The anastomosis procedure is typically performed using minimally invasive surgical techniques including laparoscopic means and instrumentation. While the procedure is shown and described using suture structures 102, it is envisioned and understood that suture structures 112 or 122 may be used equally herewith.

Figure 6:
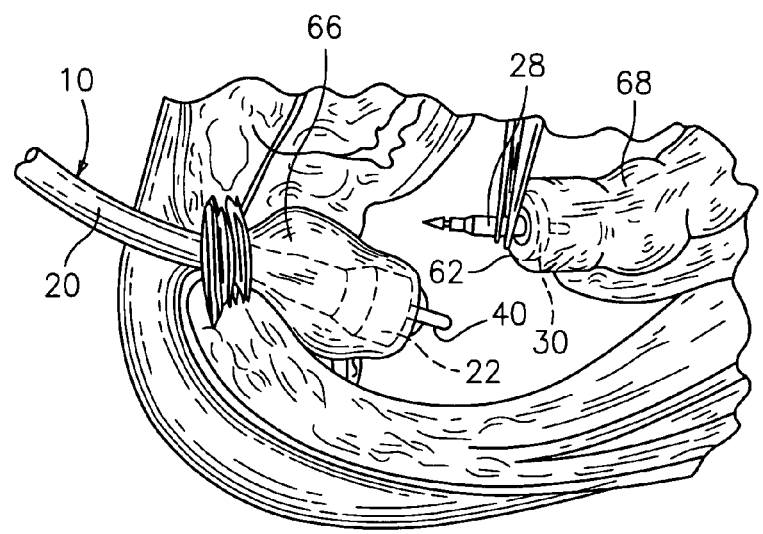
FIG. 6 is a perspective view of the intestinal area of a patient, illustrating a method of using any of the suture structures of FIGS. 2-5 in performing an anastomosis procedure.
Figure 7:
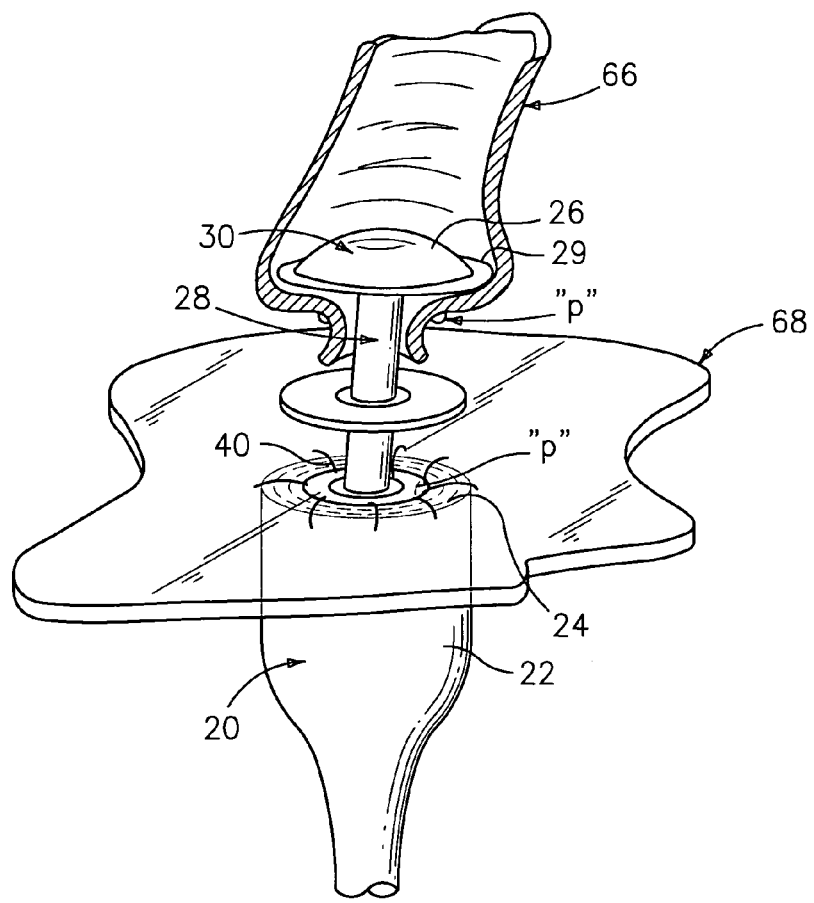
FIG. 7 is a schematic perspective view of the intestinal area of FIG. 6, illustrating the anvil shaft mounted to the connection member of the annular stapling device.
Figure 8:
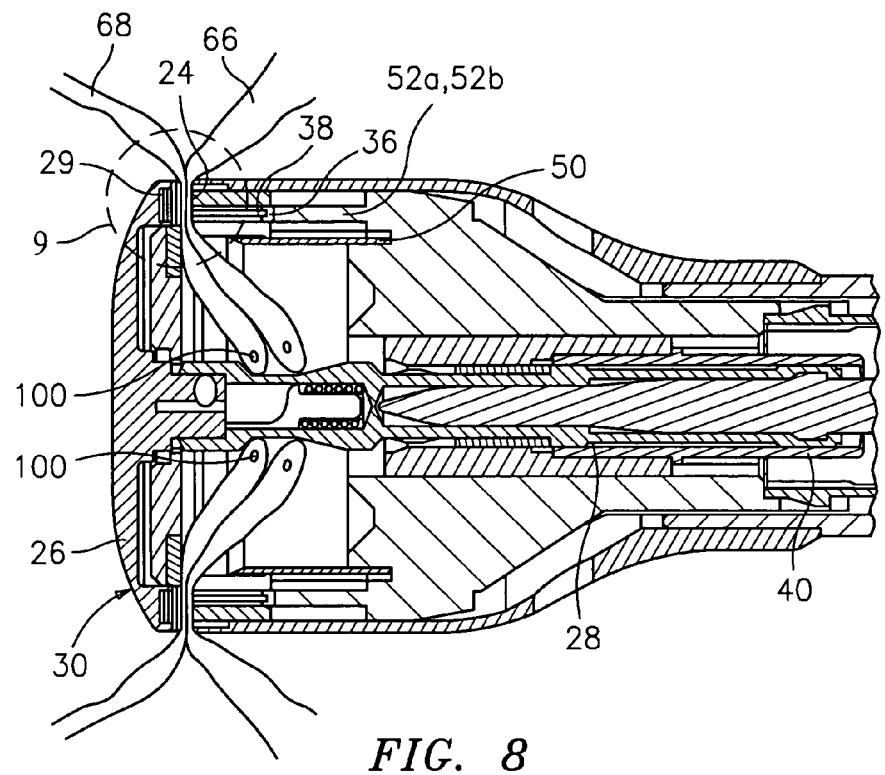
FIG. 8 is a longitudinal cross-sectional view of the distal end of the annular stapling device following approximation of the anvil member toward the staple pusher assembly.

At the point in the procedure shown in FIG. 6, a diseased intestinal section has been previously removed, anvil assembly 30 has been applied to the operative site either through a surgical incision or transanally and positioned within intestinal section 68, and tubular body portion 20 of surgical stapling device 10 has been inserted transanally into intestinal section 66. Desirably, as seen in FIG. 7, intestinal sections 66 and 68 have been temporarily secured (e.g., purse string sutured) about their respective components (e.g., shaft 28 of anvil assembly 30, and connecting member 40 of tubular body portion 20) by suture structure 102 of suture needle assembly 100. Desirably, as seen in FIGS. 7-9, when intestinal sections 66 and 68 is sutured to shaft 28 of anvil assembly 30, and connecting member 40 of tubular body portion 20, needle 110 (see FIG. 2) of suture needle assembly 100 is passed through or sewn through intestinal sections 66 and 68 in such a manner that suture structure 102 extends across staple pockets 24 of staple cartridge assembly 22 and/or across staple anvil pockets 27 of anvil member 26.

The surgeon then maneuvers anvil assembly 30 until the proximal end of shaft 28 is inserted into or otherwise operatively connected to connecting member 40 of tubular body portion 20. Thereafter, as seen in FIG. 8, anvil assembly 30 and tubular body portion 20 are approximated to approximate intestinal sections 66 and 68. Desirably, in one embodiment, as seen in FIG. 9, anvil assembly 30 is approximated toward staple cartridge assembly 22 by an amount sufficient to create a pressure on suture structure 102 sufficient to rupture suture structure 102 and release wound treatment material "W" between intestinal sections 66 and 68.

In the event that suture structures 112 or 122 are used, the wound treatment material "W" (e.g., adhesive) may be pressure activated. In this manner, in use, wound treatment material "W" is activated when the pressure between anvil assembly 30 and staple cartridge assembly 22 exceeds a threshold level or some minimum level to activate the adhesive.

Figure 9:
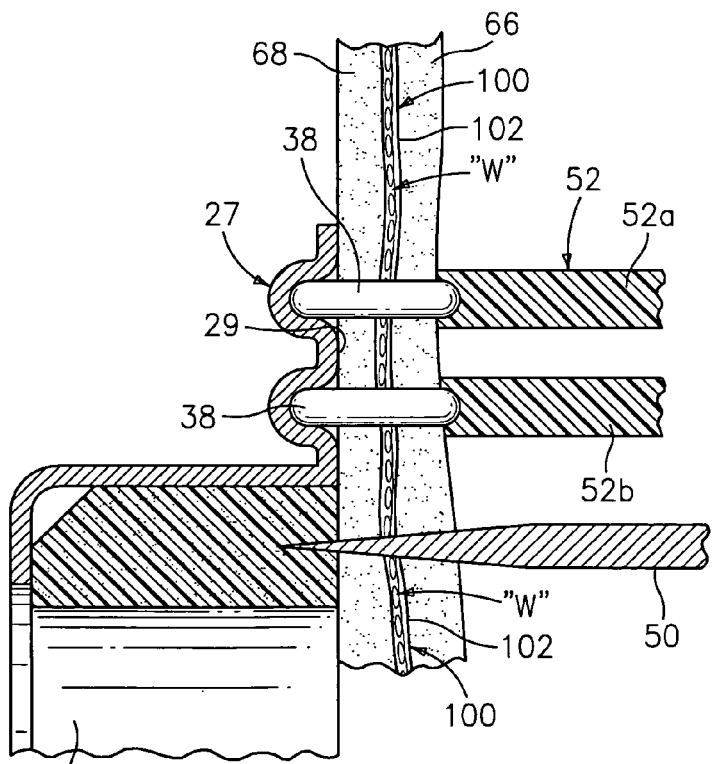
FIG. 9 is an enlarged view of the indicated area of detail of FIG. 8.

Turning now to FIG. 9, with anvil assembly 30 approximated toward staple cartridge assembly 22 and intestinal sections 66 and 68 clamped or captured therebetween, surgical stapling device 10 is fired thereby stapling and adhering intestinal sections 66, 68 to one another. Upon firing of surgical stapling device 10, staples 38 are driven from staple cartridge assembly 22 and driven through intestinal sections 66, 68 thereby mechanically securing intestinal sections 66, 68 to one another. Simultaneously therewith, knife 50 severs the portions of intestinal sections 66, 68 located radially inward of knife 50 as well as severs any portion of suture structure 102 extending across knife 50 thereby further expelling wound treatment material "W" therefrom and onto intestinal sections 66, 68.

While several particular forms of the suture structures, and a particular method of using the same, have been illustrated and described, it will also be apparent that various modifications can be made without departing from the spirit and scope of the present disclosure. For example, it is envisioned and within the scope of the present disclosure for an ultraviolet light activated wound treatment material (e.g., adhesive) to be used in connection with any of the suture structures described above. Accordingly, in use, either prior to or following firing of surgical stapling device 10, the anastomosis site is irradiated with UV light to thereby activate the adhesive.

In further embodiments, the surgical stapling device 10 is arranged for transoral introduction into the body, such as for the treatment of the esophagus.

It is further contemplated that the suture structures described herein may be used in connection with an annular surgical anastomosing device, not including any staples for securing the intestinal sections together, which is capable of approximating, adhering and cutting tissue.

Thus, it should be understood that various changes in form, detail and application of the suture structures of the present disclosure may be made without departing from the spirit and scope of the present disclosure.

What is claimed is:
1. A surgical suture, comprising:
    a suture structure including a cylindrical wall defining a single, central lumen therethrough and extending along at least a portion of a length thereof, and at least one weakened portion formed in an outer surface of the wall thereof, the weakened portion extending in a line of reduced thickness along at least a portion of the length of the wall transverse to a transverse cross-section of a circumference of the suture structure; and a wound treatment material contained within the lumen of the suture structure, the weakened portion being arranged to allow the suture structure to rupture upon application of a compressive force thereto, whereby the wound treatment material is released therefrom.

2. The surgical suture according to claim 1, wherein the wound treatment material is selected from the group consisting of adhesives, hemostats, and sealants.

3. The surgical suture according to claim 2, wherein the adhesives include materials selected from the group consisting of protein derived, aldehyde-based adhesive materials, and cyanoacrylate-based materials.

4. The surgical suture according to claim 2, wherein the sealants include materials selected from the group consisting of fibrin sealants, collagen-based tissue sealants, synthetic polymer-based tissue sealants, and synthetic polyethylene glycol-based, hydrogel materials.

5. The surgical suture according to claim 2, wherein the hemostats include materials selected from the group consisting of fibrin-based materials, collagen-based materials, oxidized regenerated cellulose-based materials, gelatin-based topical materials, and fibrinogen-thrombin combination materials.

6. The surgical suture according to claim 2, wherein the wound treatment material includes a therapeutic agent.

7. The surgical suture according to claim 6, wherein the therapeutic agents include antibiotics including materials selected from the group consisting of gentamycin sulfates, erythromycins, and derivatized glycopeptides.

8. The surgical suture according to claim 2, wherein the wound treatment materials include at least one growth promoting factor.

9. The surgical suture according to claim 8, wherein the growth promoting factor includes materials selected from the group consisting of fibroblast growth factor, bone growth factor, epidermal growth factor, platelet derived growth factor, macrophage derived growth factor, alveolar derived growth factor, monocyte derived growth factor, and magainin.

10. The surgical suture according to claim 2, further comprising a suture needle operatively connected to an end of the suture structure.

11. The surgical suture according to claim 10, where each weakened portion of the suture structure includes at least one weakening element defining a line of reduced thickness extending along the length of the cylindrical wall of the suture structure.

12. The surgical suture according to claim 11, wherein the suture structure ruptures upon application of a compressive force thereto, whereby the wound treatment material is released therefrom.

13. The surgical suture according to claim 1, wherein the suture structure is fabricated from one of a bio-absorbable material and a non-absorbable material.

14. The surgical suture according to claim 13, wherein the non-absorbable material of the suture structure is selected from the group consisting of silk, polyamides, polyesters, polyethylene terephthalate, polyacrylonitrile, polyethylene, polypropylene, silk cotton, and linen.

15. The surgical suture according to claim 13, wherein the bio-absorbable material of the suture structure is selected from the group consisting of natural collagenous materials, and synthetic resins including those derived from glycolic acid, glycolide, lactic acid, lactide, dioxanone, polycaprolactone, epsilon-caprolactone, trimethylene carbonate.

16. The surgical suture according to claim 1, wherein the single, central lumen is coaxially aligned with a central axis of the cylindrical wall.

* * * * *